United States Patent [19]  
deBenneville

[11] 4,031,186  
[45] June 21, 1977

[54] ARYLAMINOALKYLTHIOAMIDES

[75] Inventor: Peter deBenneville, Philadelphia, Pa.

[73] Assignee: Rohm and Haas Company, Philadelphia, Pa.

[22] Filed: July 10, 1975

[21] Appl. No.: 594,917

[52] U.S. Cl. .............................. 424/324; 260/551 S
[51] Int. Cl.$^2$ ............ A61K 31/165; C07C 153/063
[58] Field of Search ................. 424/324; 260/551 S

[56] References Cited

UNITED STATES PATENTS

| | | | |
|---|---|---|---|
| 3,336,381 | 8/1967 | Gilbert et al. | 260/551 S |
| 3,555,085 | 1/1971 | Welch et al. | 424/324 X |
| 3,636,015 | 1/1972 | Scanlon et al. | 260/551 S |

FOREIGN PATENTS OR APPLICATIONS

| | | | |
|---|---|---|---|
| 7,002,555 | 8/1970 | Netherlands | 260/551 S |
| 1,177,548 | 1/1970 | United Kingdom | 424/324 |

*Primary Examiner*—Frederick E. Waddell
*Attorney, Agent, or Firm*—Terence P. Strobaugh; George W. F. Simmons

[57] ABSTRACT

Arylaminoalkylthioamides and salts thereof wherein the benzene ring is substituted with halo, alkyl, lower alkoxy or 1,3-butadienylene are disclosed. The compounds are prepared by the reaction of the correspondingly substituted arylaminoalkylnitrile with hydrogen sulfide. The products are antisecretory agents useful in the treatment of ulcers.

19 Claims, No Drawings

ARYLAMINOALKYLTHIOAMIDES

This invention describes a new class of chemical compounds which can be described generally as arylaminoalkylthioamides and to the nontoxic, pharmacologically acceptable acid addition salts.

It has long been believed that decreasing the total acidity of the stomach, either by reducing the amount of gastric secretion or its acidity would stop the erosion of mucosal layer and epithelium, which constitutes an ulcer and repair processes would function. There are presently two types of drugs to bring about this condition, the antacid and the antisecretory.

The antacids offer only temporary symptomatic relief, since their effect is primarily to buffer the high concentration of acid. The antisecretory drugs do bring about the desired effect.

The mode of action of present day antisecretory drugs is to block the vagus nerve which controls gastric secretory activity. They are the chemical counterpart of a vagotomy, or interruption of the vagus nerve, which is the standard surgical treatment for ulcer. Unfortunately, the vagus nerve is part of the parasympathetic nervous system and the present day antisecretory drugs are in reality, general parasympatholytic (anticholinergic) agents. Anticholinergic drugs bring about side effects which are totally unrelated to the area in question and not very tolerable.

It has been my objective to develop a drug which would have antisecretory activity with no significant anticholinergic effect. Such a drug would either be specific for the vagus nerve or exert its effect through some route, as yet undefined, other than the parasympathetic nervous system.

Pharmacological studies show that the instant products cause a significant decrease in volume of gastric secretion and lowering of acidity in the stomach. When administered in effective therapeutic dosages, in conventional vehicles, the instant products effectively reduce the amount of gastric secretion and lower the pH of the secretion without causing significant parasympatholytic effect. The products are therefore useful in the treatment of ulcers.

The arylaminoalkylthioamides (I, infra) of this invention are compounds having the following structural formula:

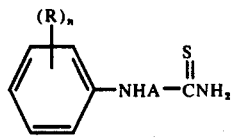

wherein A is hydrocarbylene (i.e., a divalent organic radical composed of carbon and hydrogen) containing from one to three carbon atoms, for example, lower alkylene, such as methylene, ethylene, methylmethylene, dimethylmethylene and the like or lower alkenylene, such as vinylene, methylvinylene and the like; R is the same or different radicals selected from methyl, lower alkoxy such as methoxy, ethoxy and the like, halo such as bromo, fluoro, chloro and the like or two R radicals on adjacent carbon atoms of the benzene ring may be joined together to form 1,3-butadienylene (i.e., —CH=CH—CH=CH=) and $n$ is an integer having a value of two to three.

A preferred embodiment of the invention relates to the arylaminoalkylthioamides (a, infra) having the following structural formula:

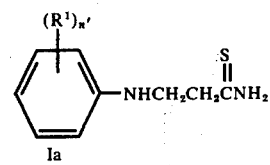

wherein $R^1$ is the same or different radical selected from methyl or chloro and $n$ is an integer of two or three. These compounds exhibit particularly good antisecretory activity.

The arylaminoalkylthioamides (I, supra) are conveniently prepared by treating the correspondingly substituted arylaminoalkylnitrile (II, infra) with hydrogen sulfide in a solvent which is inert or substantially inert to the reactants such as the N,N-di- lower alkylamino-lower alkanols, for example, N,N-dimethylaminoethanol and the like. The reaction may be conducted at a temperature from about 0° to about ambient temperature for a period of time of from about 18 hours to 30 days; however, in most instances the reaction is conveniently conducted by dissolving the arylaminoalkylnitrile in the solvent and bubbling in hydrogen sulfide at 0° C. and allowing the reaction mixture to stand for from three to five days at ambient temperature. The following equation illustrates this process:

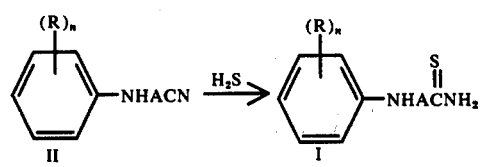

wherein A, R and $n$ are as defined above.

The arylaminoalkylnitriles (II, supra) employed in the preparation of the arylaminoalkylthioamides are either known compounds or may be prepared by treating the correspondingly substituted arylamine (III, infra) with hydroxy alkylnitrile (IV, infra) or when the compounds wherein A is ethylene is desired by employing arcylonitrile. The reaction is conducted at a temperature in the range of from about 90° to about 100° C. for a period of time from about four hours to about eight hours. When acrylonitrile is employed, a polymerization inhibitor such as hydroquinone is employed and also a catalyst such as cupric acetate is employed. The following equation illustrates this process:

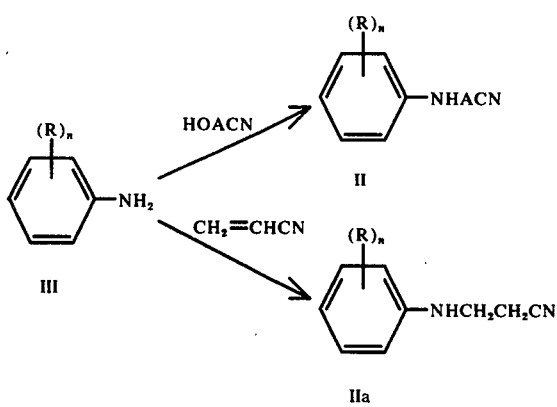

Included within the scope of this invention are the nontoxic, pharmaceutically acceptable acid addition salts of the products. In general, any acid which will form a salt with the foregoing arylaminoalkylthioamides (I, supra) and whose pharmacological properties will not cause an adverse physiological effect when ingested by the body system is considered as being within the scope of this invention. Suitable acids for preparing the salts include those derived from strong mineral acids such as hydrochloric acid, hydrobromic acid and the like.

The examples which follow illustrate the arylaminoalkylthioamides (I) of this invention and a method by which they are prepared. However, the examples are illustrative only and it will be apparent to those having ordinary skill in the art that all of the products embraced by Formula I (supra) may also be prepared in an analagous manner by substituting the appropriate starting materials for those set forth in the examples.

EXAMPLE 1

3-(2,4-Dimethylanilino)thiopropionamide)

Step A — 3-(2,4-Dimethylanilino)propionitrile

A mixture of 2,4-dimethylaniline (212 g.), acrylonitrile (80 g.), hydroquinone (0.5 g.) and cupric acetate (5 g.) is heated under reflux for 2.5 hours. The mixture is distilled to yield 127 g. of 3-(2,4-dimethylanilino)-propionitrile, b. p. 129° C./0.5 mm.

Step B — 3-(2,4-Dimethylanilino)thiopropionamide

A solution of 3-(2,4-dimethylanilino)thiopropionamide in N,N-dimethylaminoethanol (60 ml.) is cooled in an ice-bath and hydrogen sulfide (11 g.) is added. After three days at room temperature, the mixture is poured in ice-water, filtered, dried and recrystallized from benzene to yield 45 g. of 3-(2,4-dimethylanilino)-thiopropionamide, m. p. 104°–105° C.

Elemental Analysis for $C_{11}H_{16}N_2S$: Calc'd.: C, 63.4; H, 7.7; N, 13.5; S, 15.4; Found: C, 63.56; H, 7.79; N, 13.48; S, 15.10.

EXAMPLE 2

3-(4-Chloro-2-methylanilino)thiopropionamide

Step A — 3-(4-Chloro-2-methylanilino)propionitrile

A mixture of 4-chloro-2-methylaniline (35.3 g.), acrylonitrile (16 g.), hydroquinone (0.13 g.) and cupric acetate (1.25 g.) is heated three hours at 90°–95° C. The mixture is distilled to afford 23.2 g. of 3-(4-chloro-2 methylanilino)propionitrile; b. p. 150°–154° C./0.6 mm.

Step B — 4-(4-Chloro-2-methylanilino)thiopropionamide

To a mixture of 3-(4-chloro-2-methylanilino)propionitrile (23.2 g.) and dimethylaminoethanol (37.8 g.) is added hydrogen sulfide (5 g.). After three days, the mixture is poured into ice water and the solid collected by filtration is dried and recrystallized from benzene to afford 22 g. of 3-(4-chloro-2-methylanilino)thiopropionamide, m. p. 100.5° to 101.8° C.

Elemental Analysis for $C_{10}H_{13}ClN_2S$: Calc'd.: C, 52.8; H, 5.7; N, 12.3; Found: C, 5.29; H, 5.58; N, 12.04.

EXAMPLE 3

3-(2,4,5-Trimethylanilino)thiopropionamide

Step A — 3-(2,4,5-Trimethylanilino)propionitrile

A mixture of 2,4,5-trimethylaniline (27 g.), acrylonitrile (20 g.), hydroquinone (0.1 g.) and cupric acetate (0.6 g.) is heated for three hours at 90°–100° C. The mixture is distilled to afford 27 g. of 3-(2,4,5-trimethylanilino)propionitrile; b. p. 150°–165° C./0.75 mm.

Step B — 3-(2,4,5-Trimethylanilino)thiopropionamide

To a cold solution of 3-(2,4,5-trimethylanilino)propionitrile (18.9 g.) in dimethylaminoethanol (40 g.) is added hydrogen sulfide (3.5 g.). After three days at room temperature, the mixture is poured on ice and the resulting solid is collected by filtration and recrystallized from benzene to afford 14 g. of 3-(2,4,5-trimethylolanilino)thiopropionamide; m. p. 109.5°–111° C.

Elemental Analysis for $C_{12}H_{18}N_2$: Calc'd.: C, 64.9; H, 8.1; N, 12.6; Found: C, 64.9; H, 8.2; N, 12.6.

EXAMPLE 4

3-(2,3-Dimethylanilino)thiopropionamide

Step A — 3-(2,3-Dimethylanilino)propionitrile

A mixture of 2,3-dimethylaniline (61 g.), acrylonitrile (40 g.), hydroquinone (0.2 g.) and cupric acetate (1.25 g.) is heated for six hours at 95°–100° C. and the mixture then distilled to afford 57 g. of 3-(2,3-dimethylanilino)propionitrile; b. p. 138°–143° C./0.7 mm.; m. p. 65.5°–67° C.

Step B — 3-(2,3-Dimethylanilino)thiopropionamide

To a cold mixture of 3-(2,3-dimethylanilino)propionitrile (17.4 g.) and dimethylaminoethanol (24 g.) is added hydrogen sulfide (3.5 g.). After five days, the mixture is added to ice water and the resulting solid crystallized from benzene to afford 14 g. of 3-(2,3-dimethylanilino)thiopropionamide; m. p. 116°–118° C.

Elemental Analysis for $C_{11}H_{16}N_2S$: Calcd'd.: C, 63.4; H, 7.7; N, 13.5; Found: C, 62.9; H, 7.9; N, 13.3.

In a manner similar to that described in Examples 1–4, the following arylaminoalkylthioamides of this invention may be prepared. The following equation illustrates the reaction and taken together with Table I (infra) illustrates the starting materials, intermediates and arylaminoalkylthioamides obtained:

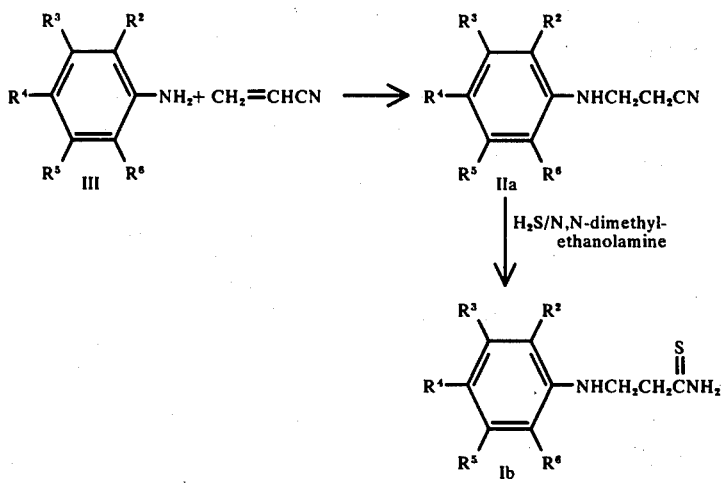

TABLE I

| Example No. | R² | R³ | R⁴ | R⁵ | R⁶ | Intermediate IIa - b.p. (or m.p.)° C. | Final Product Ib - m.p./° C. |
| --- | --- | --- | --- | --- | --- | --- | --- |
| 5 | H | CH₃ | CH₃ | H | H | 148°–150°/0.8 | 76°–77° |
| 6 | CH₃ | H | CH₃ | H | H | 129°–133°/0.5 mm. | 104°–105° |
| 7 | CH₃ | H | H | CH₃ | H | 126°–134°/0.5 mm. | 105°–106° |
| 8 | CH₃ | Cl | H | H | H | 158°–163°/1 mm. | 113°–+° |
| 9 | Cl | H | CH₃ | H | H | 145°–160°/1 mm. | 181°–182° |
| 10 | H | CH₃ | H | CH₃ | H | 148°–150°/0.8 | 62°–63° |
| 11 | CH₃ | H | OCH₃ | H | H | 163°–168°/1 mm. | 90°–91° |
| 12 | -CH=CH-CH=CH- | | H | H | H | 180°–200°/0.8 mm. | 106°–107° |

The novel compounds of this invention are antisecretory or acidity reducing drugs having no significant parasympatholytic effect which can be administered in a wide variety of therapeutic dosages in conventional vehicles. For example, by oral administration in the form of a tablet or a capsule or by intravenous injection. Also, the daily dosage of the products may be varied over a wide range varying from 5 to 500 mg. The product is preferably administered in subdivided doses in the form of scored tablets containing 5, 10, 25, 50, 100, 150, 200, 250 and 500 mg. of the active ingredient for the symptomatic adjustment of the dosage to the patient to be treated. These dosages are well below the toxic or lethal dose of the products. A suitable unit dosage form of the products of this invention can be administered by admixing 50 mg. of an arylaminoalkylthioamide (I) or a suitable acid addition salt thereof with 149 mg. of lactose and 1 mg. of magnesium stearate and placing the 200 mg. mixture into a No. 1 gelatin capsule. Similarly, by employing more of the active ingredient and less lactose, other dosage forms may be put up in No. 1 gelatin capsules and should it be necessary to mix more than 200 mg. of ingredient together, larger capsules may be employed. Compressed tablets, pills, or other desired unit dosages can be prepared to incorporate the compound of this invention by conventional methods and, if desired, can be made up as elixirs or injectable solutions by methods well known to pharmacists.

It is also within the scope of this invention to combine two or more of the compounds of this invention in a unit dosage form or to combine one or more of the compounds of this invention with known antiulcer agents or with other desired therapeutic and/or nutritive agents in dosage form.

The following example is included to illustrate the preparation of a representative dosage form.

EXAMPLE 13

Dry filled capsules containing 50 mg. of active ingredient per capsule.

| | |
| --- | --- |
| 3-(2,4-Dimethylanilino)thiopropionamide | 50 mg. |
| Lactose | 149 mg. |
| Magnesium Stearate | 1 mg. |
| Capsule (size No. 1) | 200 mg. |

The 3-(2,4-dimethylanilino)thiopropionamide is reduced to a No. 60 powder and then lactose and magnesium stearate are passed through a No. 60 bolting cloth onto the powder and the combined ingredients, admixed for 10 minutes and then filled into a No. 1 dry gelatin capsule.

Similar dry filled capsules can be prepared by replacing the active ingredient of the above example by any of the other novel compounds of this invention.

It will be apparent from the foregoing description that the arylaminoalkylthioamides (I) of this invention constitute a valuable class of compounds which have not been prepared heretofore. One skilled in the art will also appreciate the processes disclosed in the above examples are merely illustrative and are capable of a wide variation and modification without departing from the spirit of the invention.

What is claimed is:

1. A compound having the following formula:

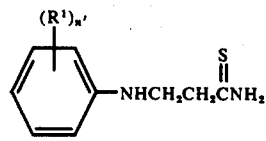

wherein $R^1$ is the same or different radical selected from methyl, methoxy, ethoxy, or chloro and $n'$ is an integer of two or three and the nontoxic, pharmacologically acceptable acid addition salts.

2. A compound according to claim 1 named 3-(2,4-dimethylanilino)thiopropionamide.

3. A compound according to claim 1 named 3-(4-chloro-2-methylanilino)thiopropionamide.

4. A compound according to claim 1 named 3-(2,4,5-trimethylanilino)thiopropionamide.

5. A compound according to claim 1 named 3-(2,3-dimethylanilino)thiopropionamide.

6. A compound according to claim 1 named 3-(3-chloro-2-methylanilino)thiopropionamide.

7. A method for treating a stomach ulcer which comprises administering to a patient in need of such treatment an effective amount of a compound of the formula:

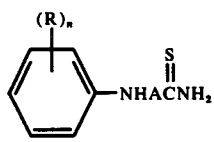

wherein A is hydrocarbylene containing from one to three carbon atoms; R is methyl, methoxy, ethoxy, halo or two R radicals on adjacent carbon atoms of the benzene ring may be joined together to form 1,3-butadienylene and $n$ is an integer having a value of two to three or the nontoxic pharmacologically acceptable acid addition salts.

8. The method of claim 7 wherein the active ingredient has the formula:

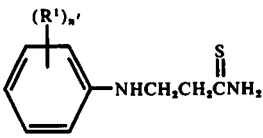

wherein $R^1$ is the same or different radical selected from methyl or chloro and $n'$ is an integer of two or three.

9. The method of claim 8 wherein the active ingredient is 3-(2,4-dimethylanilino)thiopropionamide.

10. The method of claim 8 wherein the active ingredient is 3-(4-chloro-2-methylanilino)thiopropionamide.

11. The method of claim 8 wherein the active ingredient is 3-(2,4,5-trimethylanilino)thiopropionamide.

12. The method of claim 8 wherein the active ingredient is 3-(2,3-dimethylanilino)thiopropionamide.

13. The method of claim 8 wherein the active ingredient is 3-(3-chloro-2-methylanilino)thiopropionamide.

14. A composition for treating stomach ulcers which comprises an effective amount of the compound has the formula:

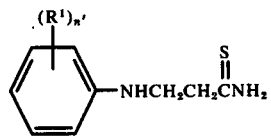

wherein $R^1$ is the same or different radicals selected from methoxy, ethoxy, methyl or chloro and $n'$ is an integer of 2 or 3 and the nontoxic, pharmacologically acceptable acid addition salts in a pharmaceutically acceptable carrier.

15. The composition of claim 14 wherein the compound is 3-(2,4-dimethylanilino)thiopropionamide.

16. The composition of claim 14 wherein the compound is 3-(4-chloro-2-methylanilino)thiopropionamide.

17. The composition of claim 14 wherein the compound is 3-(2,4,5-trimethylanilino)thiopropionamide.

18. The composition of claim 14 wherein the compound is 3-(2,3-dimethylanilino)thiopropionamide.

19. The composition of claim 14 wherein the compound is 3-(3-chloro-2-methylanilino)thiopropionamide.

* * * * *